(12) United States Patent
Pawliszyn

(10) Patent No.: US 11,092,522 B2
(45) Date of Patent: Aug. 17, 2021

(54) DEVICES TO FACILITATE SAMPLING WITH THIN FILM SOLID PHASE MICROEXTRACTION

(71) Applicant: Janusz Pawliszyn, Waterloo (CA)

(72) Inventor: Janusz Pawliszyn, Waterloo (CA)

( * ) Notice: Subject to any disclaimer, the term of this patent is extended or adjusted under 35 U.S.C. 154(b) by 253 days.

(21) Appl. No.: 15/899,223

(22) Filed: Feb. 19, 2018

(65) Prior Publication Data

US 2018/0266928 A1 Sep. 20, 2018

Related U.S. Application Data

(60) Provisional application No. 62/465,762, filed on Mar. 1, 2017.

(51) Int. Cl.
*G01N 1/40* (2006.01)
*B01L 9/00* (2006.01)
(Continued)

(52) U.S. Cl.
CPC ............... *G01N 1/405* (2013.01); *B01L 3/50* (2013.01); *B01L 3/50825* (2013.01); *B01L 9/52* (2013.01);
(Continued)

(58) Field of Classification Search
CPC .... G01N 1/405; G01N 30/06; G01N 30/8675; G01N 33/1826; G01N 1/14; G01N 30/7233; G01N 1/10; G01N 2030/009; G01N 2001/1056; G01N 2030/062; G01N 2033/184; G01N 2030/027; B01L 2300/16; B01L 2300/12; B01L 2300/042; B01L 2300/0832; B01L 2300/0618; B01L 3/50825; B01L 3/50; B01L 9/52; B01L 2200/0631; B01L 2300/069;
(Continued)

(56) References Cited

U.S. PATENT DOCUMENTS 5,364,596 A * 11/1994 Magnussen, Jr. ...... B01L 3/0224
422/515
5,792,424 A * 8/1998 Homberg .............. B01L 3/0224
422/515
(Continued)

OTHER PUBLICATIONS

Ahmadi et al., "Time Weighted Average Concentration Monitoring Based on Thin Film Solid Phase Microextraction", Environmental Science & Technology, Mar. 2017, vol. 51(7), pp. 3929-3937.
(Continued)

*Primary Examiner* — Lore R Jarrett
(74) *Attorney, Agent, or Firm* — Borden Ladner Gervais LLP; David Nauman

(57) ABSTRACT

The present invention describes several embodiments of a device that allows for the supporting, storage and deployment of large surface area thin film solid phase microextraction (TF-SPME) chemical samplers from within a sample fluid carrier. The utility of said supporting device originates from the process by which the extraction surface is stabilised within a sample carrying fluid for the extraction of chemical molecules from said sample carrying fluid. The device is also characterized by having a seating cavity, and moving mechanism or cap that can switch the supported TF-SPME chemical sampler between an open, sampling position or closed storage position.

19 Claims, 8 Drawing Sheets

(51) Int. Cl.
*B01L 3/00* (2006.01)
*G01N 1/10* (2006.01)
*G01N 30/72* (2006.01)
*G01N 1/14* (2006.01)
*G01N 30/06* (2006.01)
*G01N 33/18* (2006.01)
*G01N 30/86* (2006.01)
*G01N 30/02* (2006.01)
*G01N 30/00* (2006.01)

(52) U.S. Cl.
CPC ............... *G01N 1/10* (2013.01); *G01N 1/14* (2013.01); *G01N 30/06* (2013.01); *G01N 30/7233* (2013.01); *B01L 2200/0631* (2013.01); *B01L 2200/0689* (2013.01); *B01L 2300/042* (2013.01); *B01L 2300/045* (2013.01); *B01L 2300/069* (2013.01); *B01L 2300/0618* (2013.01); *B01L 2300/0832* (2013.01); *B01L 2300/0861* (2013.01); *B01L 2300/12* (2013.01); *B01L 2300/16* (2013.01); *G01N 30/8675* (2013.01); *G01N 33/1826* (2013.01); *G01N 2001/1056* (2013.01); *G01N 2030/009* (2013.01); *G01N 2030/027* (2013.01); *G01N 2030/062* (2013.01); *G01N 2033/184* (2013.01)

(58) Field of Classification Search
CPC ..... B01L 2300/0861; B01L 2200/0689; B01L 2300/045
See application file for complete search history.

(56) References Cited

U.S. PATENT DOCUMENTS

| | | | |
|---|---|---|---|
| 6,042,787 A * | 3/2000 | Pawliszyn | B82Y 30/00 |
| | | | 422/430 |
| 6,588,255 B2 | 7/2003 | Pawliszyn | |
| 6,871,557 B2 * | 3/2005 | Magnussen, Jr. | B01L 3/0279 |
| | | | 422/522 |
| 6,941,825 B2 | 9/2005 | Pawliszyn | |
| 7,384,794 B2 | 6/2008 | Pawliszyn | |
| 7,674,631 B2 * | 3/2010 | Pawliszyn | G01N 1/40 |
| | | | 422/500 |
| 8,286,511 B2 * | 10/2012 | Burken | G01N 1/08 |
| | | | 73/863.21 |
| 8,598,325 B2 | 12/2013 | Pawliszyn | |
| 2005/0014156 A1 * | 1/2005 | Pawliszyn | G01N 1/40 |
| | | | 435/7.23 |
| 2005/0276727 A1 * | 12/2005 | Pawliszyn | A61B 5/417 |
| | | | 422/537 |
| 2009/0277283 A1 * | 11/2009 | Burken | G01N 1/405 |
| | | | 73/863.21 |

OTHER PUBLICATIONS

Grandy et al., "Development of a Carbon Mesh Supported Thin Film Microextraction Membrane as a Means to Lower the Detection Limits of Benchtop and Portable GC/MS Instrumentation", Analytical Chemistry, Feb. 2016, vol. 88(3), pp. 1760-1767.

Jiang and Pawliszyn., "Thin-Film Microextraction Offers Another Geometry for Solid-Phase Microextraction", TrAC Trends in Analytical Chemistry, Oct. 2012, vol. 39, pp. 245-253.

Riazi Kermani and Pawliszyn., "Sorbent Coated Glass Wool Fabric as a Thin Film Microextraction Device", Analytical Chemistry, Oct. 2012, vol. 84 (21), pp. 8990-8995.

Piri-Moghadam et al., "Review of Geometries and Coating Materials in Solid Phase Microextraction: Opportunities, Limitations, and Future Perspectives", Analytica Chimica Acta, Sep. 2017, vol. 984, pp. 42-65.

Piri-Moghadam et al., "Inter-laboratory Validation of a Thin Film Microextraction Technique for Determination of Pesticides in Surface Water Samples", Analytica Chimica Acta, Apr. 2017, vol. 964, pp. 74-84.

* cited by examiner

DEVICES TO FACILITATE SAMPLING WITH THIN FILM SOLID PHASE MICROEXTRACTION

FIELD OF THE INVENTION

The presented invention relates to methods of sampling and sample storage in the field of analytical chemistry for the analysis of small organic molecules by GC-based or LC-based instrumentation. The device acts as a holder and housing, offering support for a thin film solid phase microextraction chemical sampler allowing for the deployment and storage of said chemical sampler.

BACKGROUND OF THE INVENTION

Thin film solid phase microextraction (TF-SPME) refers to a division of solid phase microextraction (SPME) by which a solid extraction surface (sorbent) is arranged in such a way that there is a relatively larger surface area available for contact with the sample matrix in relation to the total sorbent volume to perform the non-exhaustive extraction of small organic molecules. The sorbent can be supported on appropriate surface or self-supported. The general description of the concept of TF-SPME was described in U.S. Pat. No. 6,588,255 issued on Jul. 8, 2003 and U.S. Pat. No. 6,941,825 issued on Sep. 13, 2005 while in this application devices used in combination with TF-SPME are described facilitating important applications. SPME techniques are generally well known to persons skilled in the art and thus do not require detailed description herein. Briefly, both SPME and TF-SPME allows for the enrichment of small organic molecules onto a solid extraction phase which can then be desorbed using heat or solvent from said extraction phase for chemical determination. This determination is classically performed using hyphenated gas chromatography (GC) or liquid chromatography (LC) techniques. More recently matrix compatible solid extraction phases have been developed and described in U.S. Pat. No. 7,384,794 issued Jun. 10, 2008 and U.S. Pat. No. 8,598,325 issued Dec. 3, 2013. These coatings facilitated enrichment of small organic molecules present sample fluid carrier and therefore for the increased sensitivity of said small organic molecules while eliminating interferences posed by larger sample matrix components present in the fluid carrier. Classically, SPME devices have been viewed as a solid phase extraction surface coated onto a cylindrical fibre. However, the solid phase micro extraction process may also be performed using a sorptive coating of thin sheets, discs, stir bars, capillary tubing, and even loose particles geometries. For each of these varied geometries, appropriately designed holders are required to facilitate facile and reliable sampling and post-sampling storage. As such, novel embodiments of these holders are described herein.

SUMMARY OF THE INVENTION

In one embodiment of the invention a retracted thin film solid phase microextraction blade device was developed which incorporated as the extraction surface a hydrophilic lipophilic balance—polyacrylonitrile (HLB—PAN) for broad range polarity compound extraction (MLB) imbedded in a matrix compatible (PAN) binder as well as C18-PAN for hydrophobic extraction (octadecyl derivatized silica C-18) imbedded in PAN binder allowing for time weighted average (TWA) based sampling. This embodiment, shown in FIG. 1 was constructed by placing a thin film microextraction blade (100) containing zone of extraction surface in form of high surface area thin film extraction coating (102) within a polytetrafluoroethylene (PTFE), (Teflon) supporting holder (112), which was then placed in a biofouling preventing copper housing (108) containing a small diameter open channel (110) along with a PTFE spacer (104) which, when combined with said small diameter open channel provides an open tubular end to set the diffusion path length. A movable cap (114) could then be placed on either end of the biofouling copper housing (108) facilitating an open sampling position and closed sample storage position. Uptake of the targeted analytes was validated to remain linear for up to 70 days in-lab with the use of the standard UV blocking agents in a simulated river system. The retracted device was then successfully deployed on-site for 90-day time periods in wastewater-affected portions of the Grand River, Ontario, Canada. Open bed grab samples were also performed to cross validate the results, with good agreement obtained between the methodologies.

In another embodiment of the invention an in-bottle TF-SPME apparatus was shown which incorporated carbon mesh as a support fully covered with divinylbenzene-polydimethylsiloxane (DVB/PDMS) coating resulting in TF-SPME membranes, for the long duration equilibrium extraction of aqueous contaminants. DVB polymer particles acted as sorbent for analytes present in sample fluid carrier and PDMS act as binder forming the matrix compatible morphology. This embodiment (200), shown in FIG. 2 was constructed by hanging a TF-SPME membrane (212) on a supportive, and chemically inert fluorocarbon string (208) which was held in position by a stabilizing tin sinker (216) which was all attached to, and capped by, a PTFE sealing cap (204). A rigid stainless steel clip or pin may be used instead of the fluorocarbon string and stabilizing tin sinker. This assembly was then placed in a glass bottle carrying housing (220) where the TF-SPME extraction surface was allowed to interact with the sample fluid to perform physiochemical extraction of small organic molecules from said sample fluid. Uptake of the targeted analytes was validated to be analytically accurate by spiking clean river water samples with pure analytical standards within said in-bottle TF-SPME apparatus. The in-bottle TF-SPME apparatus was then successfully deployed along multiple pesticide affected river locations in Ontario, Canada with said in-bottle TF-SPME approach shown to be a very sensitive approach. Another embodiment involves a drill based TF-SPME approach (236), where several thin film coated film carbon mesh membranes are attached to a device with ability to be connected to a rotation mechanism. Several thin film devices can be used in a bottle device to provide higher sensitivity and/or ability to repeat measurement. Furthermore, this embodiment could also be compared in lab by attaching the thin film membrane (212) to a magnetic stir bar (232) by use of supportive clips, (228), resulting in a magnetic stirring TFME device (224). The membrane can be also attached by means of glue or screws.

In an additional embodiment of the invention, a magnetic locking coated bolt TF-SPME device was shown which incorporated a zone of HLB/PAN coating (310) as a thin film onto a stainless steel bolt or screw (308) surface acting as support for the long term storage of extracted chemical compounds on the extractive surface. This embodiment, shown in FIG. 3 was constructed by recessing rare earth magnets (312) deep within two halves of a chemical resistant solid PTFE housing (336). These magnets were only separated by 0.50 mm of PTFE when engaged in die open, sampling position (300). Slight pressure can be applied to the push rod (324) to force these magnets apart allowing the internal stainless steel spring (320) to hold the housing and scaling nut in the closed position (304). When in this closed position the extraction phase coated zone (310) of the supportive surface (308) is sealed within the open tubular sealing cavity enclosing a stable carrying fluid for long-term extract storage. Other features of this embodiment include a protective raised top (316) which has had an eye drilled into it (332) to allow the attachment of rope or a carabiner and a gripping ridge (328) to facilitate easier handling. This embodiment of the invention was then shown to successfully stabilize chemical compounds extracted from the outflow of a wastewater treatment facility in Ontario, Canada facility for up to 12 days at room temperature.

Shown in FIG. 4 a further modification of this embodiment was successfully developed to allow for deployment via remotely operable submarines at deep sea hydrothermal vents. Much like the embodiment described by FIG. 3, a heat and chemical resistant PTFE body (412) was used to protect the extraction surface within an enclosable tubular sealing cavity (408) during transportation by the submarine and storage. Furthermore, the ROV could apply pressure to the raised top of the housing (404) to move said housing into the open, sampling position, exposing the sample fluid carrier to the zone of the extraction surface (424) located on the surface of supportive bolt or screw (420). Following completion of sampling, pressure could be removed from the ROV manipulator allowing for the PTFE coated spring (416) to automatically return the sampler housing to the closed position thus protecting the extraction surface coated zone (424) of TF-SPME bolt back into the tubular sealing cavity for storage. This embodiment of the invention was then successfully deployed at two hydrothermal vent location along the Pacific Rim for the differentiation of significant chemical features between said hydrothermal vent sites and the ambient ocean waters.

DETAILED DESCRIPTION OF THE INVENTION

Figure 1:
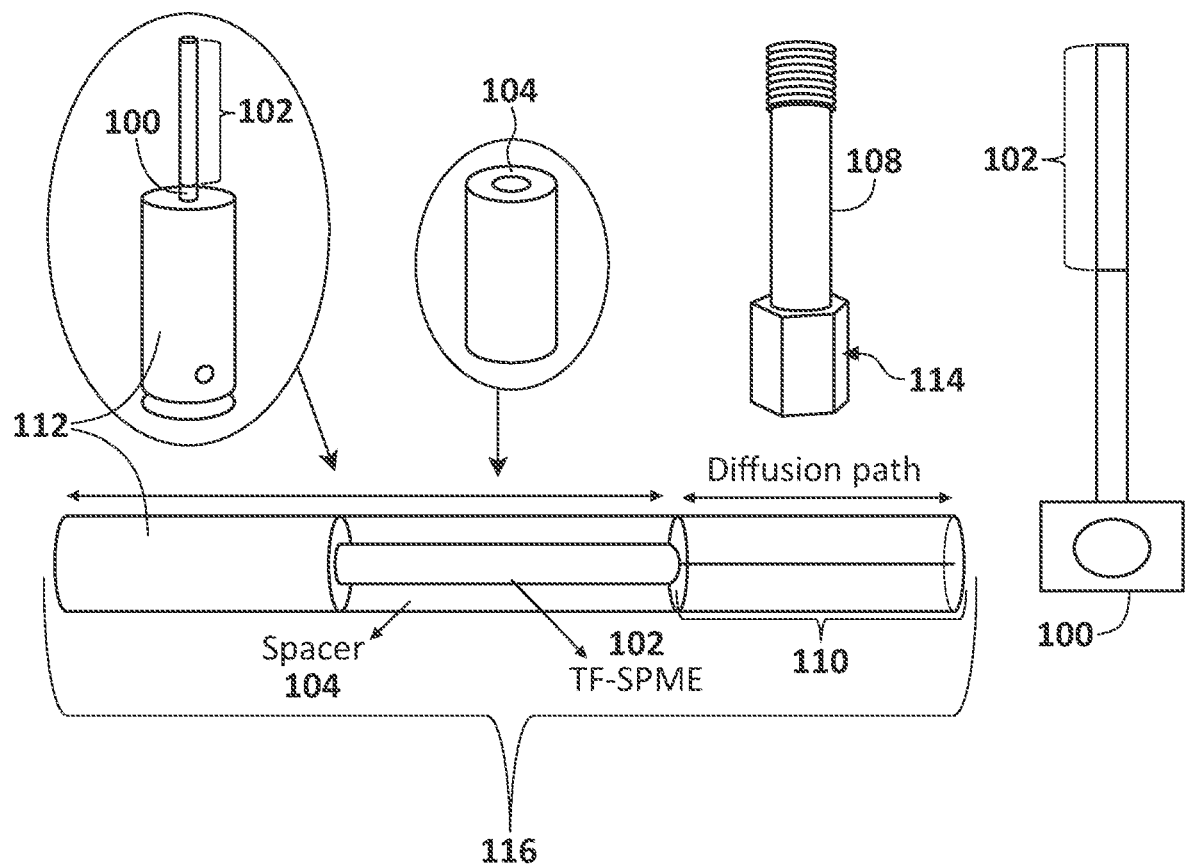
FIG. 1 Retracted TF-SPME TWA sampler with; (100): Open bed TF-SPME blade, (102): coated zone of TF-SPME blade containing extraction surface, (104): open tubular PTFE spacer, (108): copper housing tube with a drilled tubular hole as diffusion path (110), that can sealed with, (114) a removable cap, (112): a supporting PTFE rod assembly holding TF-SPME blade, all assembled into the completed retracted TWA-TFME device (116).

The following descriptions will now detail the intricacies and validation of the invention in a manner that shall be comprehensible to those skilled in the art. It is important to note that the subsequent description is meant to be encompassing of the current configuration of the invention and should not be perceived to narrow the claims that follow.

The materials used in the preparation and validation of the presented embodiments of the invention were obtained from the following sources. Nano pure water was obtained using a Barnstead/Thermodyne Nanopure ultra-pure water system (Type I water grade; for method development. Standards octyl methoxycinnamate (OMC), benzophenone-1 (Ben-1). benzophenone-2 (Ben-2), benzophenone-3 (Ben-3), benzophenone-4 (Ben-4), 2-phenylbenzimidazole-5-sulfonic acid (PBSA), oclocrylene (OCR), butyl-methoxy-dibenzoyl-methane (BM-DBM), triclosan (TCS), and triclocarban (TCC), were purchased from Sigma (Oakville, ON. Canada). The internal standard (IS) 2-hydroxy-4-metboxy-benzophenone-2',3',4',5',6'-d5 (Ben-3-d5) was obtained from CDN isotopes (Pointe-Claire, QC, Canada). C18 (5 .mu.m in diameter) particles were supplied by Supelco, and Chromabond polystyrene-divinylbenzene-weak anion exchange (PS-DVB-WAX, Macherey-Nagel) particles were obtained from VWR International (Mississauga, Canada).

Coated blades consisting of either HLB, PS-DVB-WAX, or C18 particles were prepared in lab using methods thoroughly described in scientific literature. Individual stock solutions were prepared either in methanol (Ben-1. Ben-2, Ben-3, Ben-4, TCS, TCC, OCR, OMC and BM-DBM), or in ultra-pure water with the addition of a few drops of 2 M sodium hydrogen carbonate (in the case of PBSA) at a 2 mg/mL concentration. Mixed standard solutions were prepared at a 100 .mu.g/mL concentration and stored at 4 .degree. C. Pesticide mixtures, including triazines, organophosphorus pesticides (OPPs), and carbamates in acetonitrile (ACN), were purchased from AccuStandard (New Haven, Conn., USA). Pure standards of chlorophenols, trifluralin, and methyl parathion were obtained from Sigma-Aldrich (Oakville, ON, Canada). Internal standards, including 3, 5-dichlorophenol-d3, trifluralin-d14 and metolachlor-d6, and diazinon d-10 were prepared from CDN Isotopes (Pointe-Claire. QC, Canada). DVB particles (5 .mu.m diameter) and high-density PDMS, used in the in-lab preparation of the mesh supported membranes, were obtained from Supelco (Bellefonte. Pa. U.S. A). A mixture of standards at different concentrations was prepared in ACN by diluting stock solutions for preliminary experiments, method development, and preparation of calibration levels. The MS grade methanol, acetonitrile, and water were obtained from Fisher Scientific Canada (Ontario Canada), while the salts formic acid and ammonium acetate were purchased from Sigma-Aldrich (Oakville, ON, Canada). The dimethylformamide (DMF), 150 Kdalton polyacrylonitrile (PAN) and hydrochloric acid used to prepare the coated devices were also purchased from Sigma-Aldrich. The 18-8 stainless steel nuts, bolts, and springs were purchased from Spaenaur (Kitchener, ON, Canada). The PTFE coated springs (Swagelok model 177-R3A-KI-B) were purchased from Swagelock Inc. (Sarnia, ON, Canada). The rare earth magnetics were purchased from Lee Valley Tools (Waterloo ON, Canada) The PTFE sampler bodies were sourced and constructed by the University of Waterloo Science Machine Shop (Waterloo ON, Canada) Plastic 300 .mu.L vials and amber 2 mL glass vials along with pre-pierced PTFE/silicone septa used in puncture tests were purchased from Canadian Life Sciences (Peterborough, ON, Canada). The hydrophilic-lipophilic balanced (MLB) particles used were obtained from Waters (Wilmslow. U.K.).

The design of the retracted TF—SPME TWA sampler is illustrated in FIG. 1 The sampler consisted of a copper tube to serve as the housing (108), copper caps (114) to close and seal the extraction surface in the tubular cavity of the housing (110) following a given sampling, a supporting PTFE rod assembly (112), a PTFE spacer (104) that provides an open tubular end to set the diffusion path length in conjunction with the drilled tubular cavity (110) of the copper housing (108) for TWA sampling, and a MLB/PAN TF-SPME blade (100) made in the laboratory. The copper tube was made from a copper rod that was drilled, creating a hole with a 0.76 mm inner diameter and 10.0 mm length (diffusion path). To avoid the trapping of air bubbles in the sampler, all parts of the sampler were assembled under ultrapure water. Assembly of the sampler was conducted by first locating the PTFE spacer inside the copper tube, followed by insertion of the thin film on the PTFE holder inside the copper lube, and finally, tightly screwing the cap to fix the TF-SPME in place. The sampler was then removed from the ultrapure water basin and transferred to the sampling chamber. In order to perform TWA sampling with retracted TF-SPME, three basic prerequisites have to be met. First, the coating of the TWA sampling device should act us a zero sink for all of the analytes under study, and the mass uptake rate should not be influenced by the amount of analyte already sorbed. The zero sink behavior of the coating was validated by a simple test whereby the TF—SPME devices were exposed to the aqueous standard generation in two separate modes: continuous and intermittent exposure. For continuous exposure, the selected analytes were extracted for 180 min from the aqueous standard generator before being exposed to pure water for 60 min. As for intermittent exposure, 60 min of extraction from the aqueous standard generator was followed by exposure of the TF-SPME device into pure water for 60 min. The intermittent exposure process was repeated three times and results of both exposure modes were compared. The difference between extracted amounts from both exposure modes was negligible, therefor proving the zero sink nature of the coating. The second requirement is that the passive sampler should respond proportionally to changes in analyte concentrations at the face of the device. The capability of the device to integrate high peak concentrations is an important function of any passive sampler. The third condition is that the bulk concentration of analytes must be equal to the concentration of analytes at the face of the device. The overall mass transfer resistance of the analyte from the bulk of the samples to the collecting medium should be limited to the diffusion path of the sampler.

Figure 2:
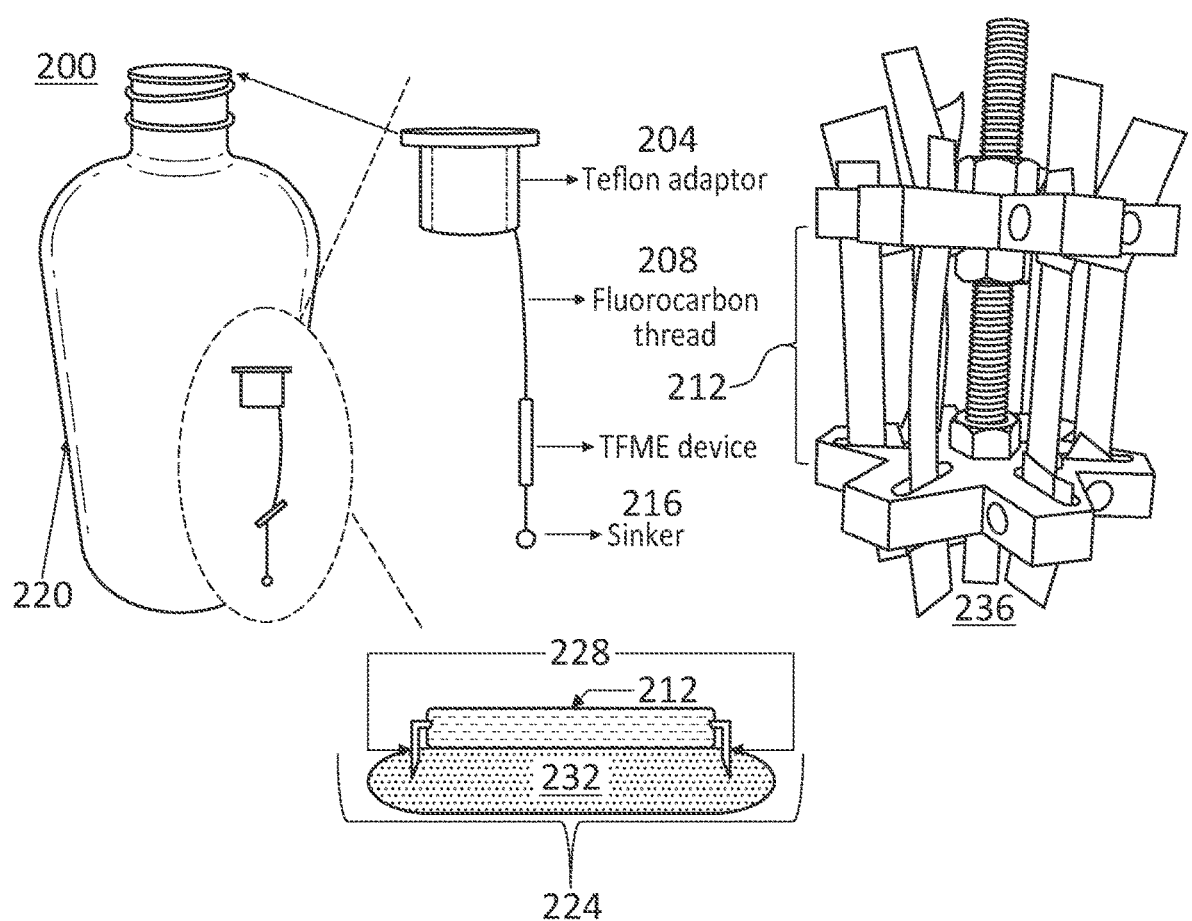
FIG. 2 In bottle TF-SPME sampling strategies showing required components of the assembled device (200) such as; (204): a movable PTFE cap, (208): a supporting fluorocarbon string, (212): the TF-SPME device, (216): a stabilizing tin sinker all contained within a glass bottle sealing cavity (220). Also (220): a comparative open bed TF-SPME holder designed for use with a power-drill and (224): a magnetically stirring open bed TFME device.

The design of the in bottle TF-SPME embodiment of the invention as shown in item (200) of FIG. 2 shows the entirety of the apparatus designed for the in-bottle TFME strategy, including a 1 L bottle (220) equipped with a PTFE home-built capping adaptor (204), which was employed to hold the membrane in the bottle through the use of a disposable fluorocarbon supportive thread (208) (Berkely fishing line) that was stabilized with a tin sinker (216). A PDMS/DVB thin film coated onto carbon mesh fabric (212) was used for evaluation of the developed methods (More information regarding preparation PDMS/DVB thin films can be found in prior art and literature and is henceforth not described herein). The bottle was filled with nano pure water for method development, while surface water was utilized in real sample analyses. The comparative employed sampling strategy consisted of the application of on-site TF-SPME via a portable sampling case, or power drill, which are capable of controlling the speed and time of agitation. Such a drill apparatus was equipped with a head to hold the multiple TFME devices simultaneously (236). The designed on-site sampling apparatus provides higher agitation rates (up to 4500 rpm), facilitating on-site extractions from river waters. If we wished to perform such comparison in the laboratory instead a magnetically stirred thin film microextraction device such as that shown in schematic (224) could be constructed by attaching the thin-film microextraction device (212) to a magnetic stir bar (232) by use of steel or polymer clips (228) or glue.

Figure 3:
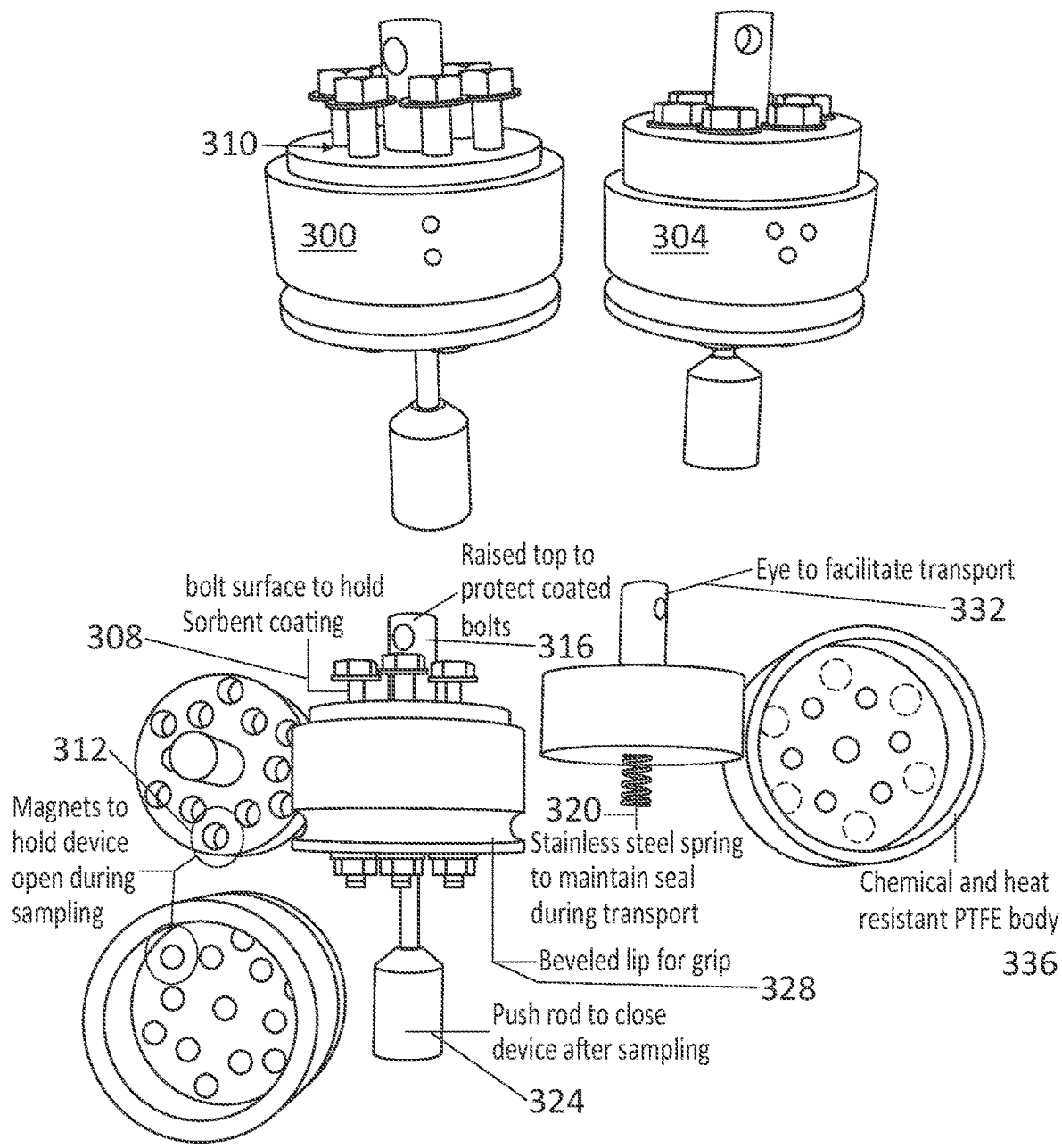
FIG. 3 Magnetic locking coated bolt TF-SPME device shown in; (300): open, sampling position and, (304): closed, sample storage position. Further breakdown of the device shows, (308): the supportive surface for the attachment of the extraction surface, (310) said extractive surface coated zone, (312): embedded magnets that hold the housing open during sampling, (316): Raised top to protect extraction surface support during sampling, (320): stainless steel spring to hold sampler housing closed during storage, (324): push rod to press the sampler housing closed, (328) bevelled grip, (332): drilled eye for rope or carabiner attachment and, (336): the heat and chemical resistant PTFE housing.
Figure 4:
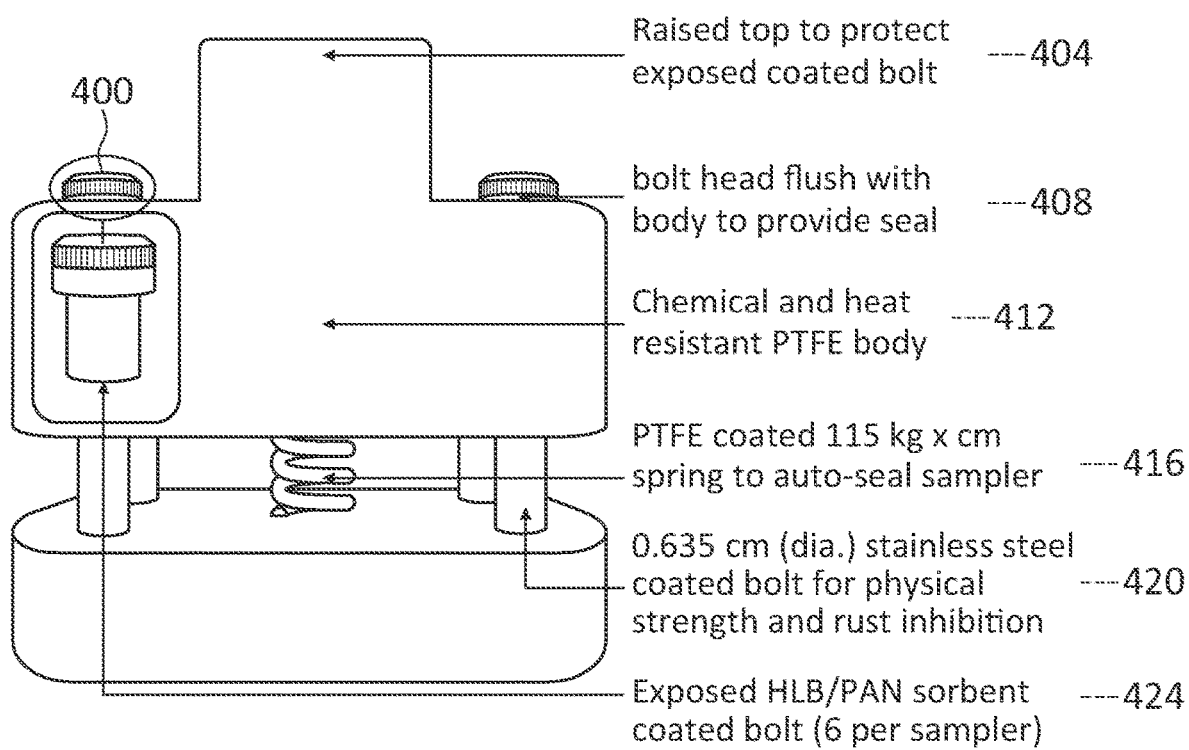
FIG. 4 Self-locking coated bolt TF-SPME device (400) enabling remotely operated vehicle (ROV) operation detailing, (404): raised top for ROV manipulator pressure application to open the tubular cavity for sampling, (408): bolt head flush with sampler housing to enclose extraction surface in tubular sealing cavity while in closed position, (412): Chemical and heat resistant PTFE housing, (416): PTFE coated spring to return housing and capping bolt to closed position, (420): the supportive bolt, (424): extraction surface coated zone in the open sampling position.

The magnetic locking and self-sealing coated bolt TF-SPME embodiments of the invention, shown in FIG. 3 and FIG. 4 respectively were designed to enable reliable post sampling analyte storage at ambient conditions. Furthermore, to facilitate easy handling by divers and deep sea ROV submersibles these SPME bolts were built into self-sealing PTFE bodied housings (336, 412). It is important to note that a screw could be used instead of a bolt. Appropriately the magnetically locking embodiment was shown to stabilize compounds originating from a wastewater treatment facility on the sorbent coating for up to 2-weeks when stored at ambient conditions. The ROV operable embodiment was successfully on two different ROV submersibles several kilometers deep at deep ocean hydrothermal vents along the Pacific Rim. In order to survive the harsh environment imposed by the deep ocean hydrothermal vent sampling regions many design considerations needed to be optimized during the construction of the ROV-TF-SPME sampler. First and foremost the device needed to be designed in a way such that it could be easily understood by the ROV pilot and reliably handled using various ROV manipulators. Furthermore, it was essential that the device could withstand temperatures of superheated water well in-excess of 100° C., maintain a high degree of chemical resistance to the highly acidic plumes, and be able to equalize and withstand water pressure at depths exceeding 2 km (199 atm), Furthermore, it was important that the bolts could be exposed solely by the employment of a squeezing motion of the ROV manipulator.

Appropriately, the HLB/PAN coated bolt ROV-TF-SPME self-sealing sampler, as shown in FIG. 4, was designed with all of these aforementioned requirements in mind. Firstly, in-addition to having a solid, compression resistant housing (412), no region on the sampler was designed to have tightly sealed void volumes ensuring the device could equalize to the ambient pressure at depth. Furthermore, by employing a solid PTFE housing (412) and PTFE coated springs (416) the sampler was designed to survive temperatures in excess of 300° C., and exhibit minimal extraction or modification by chemical species in the sampling environment. Another important aspect of the sampler was the spring assisted self-sealing design. As the ROV manipulator was limited to one axis of movement (squeezing) to toggle the device between the "open", sampling (424) and "closed", storage (408) positions it was important that the device could be self-sealing such that the HLB-PAN coatings were protected from convection of the surrounding environment after sampling was completed. This design requirement was accomplished by positioning a heavy 115 kg×cm (spring constant) PTFE coated spring at the center of the device which, upon releasing tension from the ROV manipulator, would force the two PTFE blocks apart, forcing the head of the coated bolts to sit flush against the top of the PTFE body (408) effectively protecting the sorbent coating from convection and open bed diffusion (the incorporation of the six, large diameter, 0.635 cm thick, coated 18-8 stainless steel bolts (420) directly within the sampler body was also advantageous. In addition to providing the sampler with superb physical strength under load, the diameter of the coated bolts also provided a major increase in the available surface area of the sorbent coating. As can be seen in Table 1 below out of all of the current SPME-HPLC morphologies, the coated bolt format contains the largest amount of available sorbent and, more importantly, surface area. This large, 250 mm$^2$ surface area is needed to attain adequate sensitivity during the short sampling times available within the costly ROV dive lime. As sampling times were expected to be 10 minutes or less it was expected that the extraction of most analytes would be in the pre-equilibrium regime where sensitivity is dictated by surface area. As such, a factor of 22 times signal improvement was expected over a comparable HLB/PAN SPME fiber. Furthermore, with dimensions of 8 cm×5 cm×7 cm (W×D×H), this 6 replicate sampler was constructed to minimize the space requirements on the ROV submersible during the dive. Following the successful construction and the first deployment of these ROV-TF-SPME samplers this self-sealing design was slightly modified for the sampling of shallow waters by divers and light watercraft. This modified embodiment, shown in FIG. 3, incorporates a magnetic locking system (312) such that the sampler can be held open during sampling (300). Once sampling is complete the diver can simply press on the push rod (324) such that the magnets are separated and the spring (320) can hold the device in the closed position (304) protecting the extraction surface coated zone (310) of the stainless steel supportive bolt (308). As pressure equalization considerations were not as critical, this embodiment was constructed much more tightly to further improve long-term storage of extracted compounds. Notwithstanding these modification other aspects of the diver operable sampler remain quite similar the ROV-SPME variant.

Following the successful construction and the first deployment of these ROV-TF-SPME samplers this self-sealing design was slightly modified for the sampling of shallow waters by divers and light watercraft. This modified embodiment, shown in FIG. 3, incorporates a magnetic locking system (312) such that the sampler can be held open during sampling (300). Once sampling is complete the diver can simply press on the push rod (324) such that the magnets are separated and the spring (320) can hold the device in the closed position (304) protecting the extraction surface coated zone (310) of the stainless steel supportive bolt (308). As pressure equalization considerations were not as critical, this embodiment was constructed much more tightly to further improve long-term storage of extracted compounds. Notwithstanding these modification other aspects of the diver operable sampler remain quite similar the ROV-SPME variant.

Figure 5:
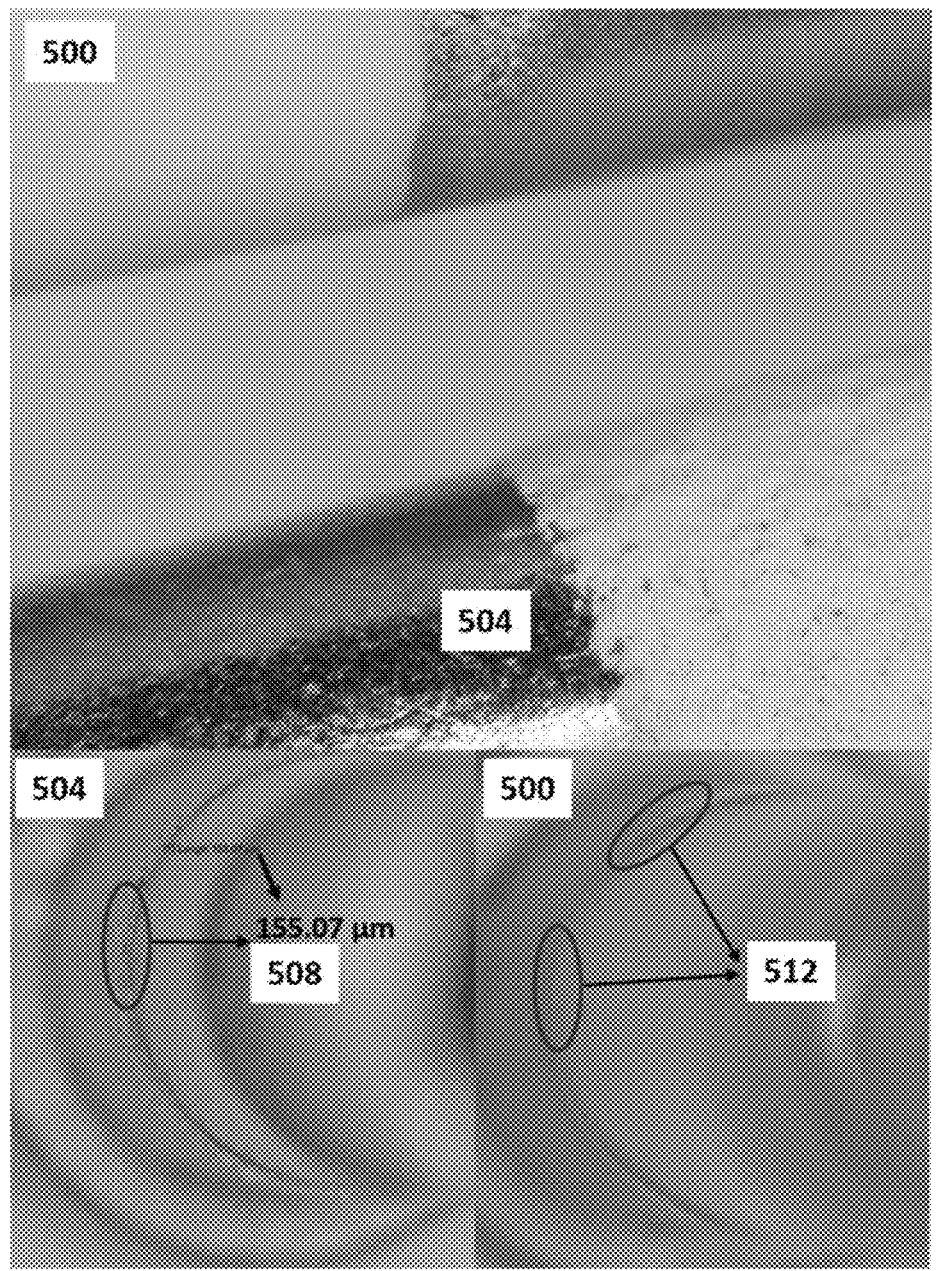
FIG. 5 Comparison of, (500): recessed coating TF-SPME bolts and, (504): non-recessed coating TF-SPME bolts highlighting, (508) top down view of the coated bolt highlighting the fragile 155 μm exposed edge of the non-recessed bolt, and (512): top down view of the recessed coated bolt highlighting the smooth transition between the sorbent coated zone and non-coated bolt support.

The coated bolts themselves, shown in FIG. 5, can be considered a unique SPME morphology that required proper optimization. Initially, the TF-SPME bolts used in the first set of ROV-TF-SPME samplers were prepared using a spray coating method to form the coated zone (504). Although functional, it was later found that these coatings were prone to stripping when returning into the open tubular end of the housing. This stripping was caused by the leading edge of the sorbent coating (508) catching on the edge of the cylindrical walls of the PTFE sampler housing when operated. To address this limitation it was decided to employ a recessed coating methodology which resulted in a coated surface possessing a diameter equal to or less than the unetched portions of the stainless steel bolt (512). Partly due to the smaller 5 μm HLB particles, the recessed coating method (500) was found to give a much smoother and uniform coating. Furthermore, as the leading edge of the sorbent coating was protected within the recession it could no longer catch on the cylindrical edge of the PTFE sealing body. Although these coatings were much thinner, containing less sorbent volume than the previous design the available surface area was relatively identical. Hence, for the short extraction times used during ROV samplings extraction efficacy should not be affected. The recessed coating approach was described in USPTO application U.S. Ser. No. 15/447,023.

TABLE 1

Comparative physical dimensions of coated HPLC SPME fibers, TFME blades, and the coated bolt sampler

|  | Coated Dia. | Coating Thickness | Coating length | Coating Vol. | Coating S.A. |
| --- | --- | --- | --- | --- | --- |
| HPLC SPME fiber | 0.27 mm | 45 μm | 1.5 cm | 0.39 mm$^3$ | 11.1 mm$^2$ |
| TFME blade | 2.55 mm* | 120 μm | 2 cm | 12.2 mm$^3$ | 102 mm$^2$ |
| Coated bolt (spray) | 6.65 mm | 150 μm | 1.2 cm | 37.3 mm$^3$ | 251 mm$^2$ |

TABLE 1-continued

Comparative physical dimensions of coated HPLC SPME
fibers, TFME blades, and the coated bolt sampler

|  | Coated Dia. | Coating Thickness | Coating length | Coating Vol. | Coating S.A. |
|---|---|---|---|---|---|
| Coated bolt (recessed) | 6.40 mm | 25 μm | 1.2 cm | 6.2 mm$^3$ | 241 mm$^2$ |

*Coated width of blade

Fittingly, maximization of surface area has been the ongoing objective of many thin-film solid-phase microextraction (TF-SPME) approaches used for on-site sampling. This is because when sampling times are short the amount of analyte extracted as a function of time $$\left(\frac{dn}{dt}\right)$$

is directly proportional to surface area (A) and does not depend and sorbent volume or strength (Eq. 1) It is important to clarify however that a weak sorbent will not remain in this linear, pre-equilibrium regime for very long, hence a strong sorbent is still important to ensure this assumption remains correct.

$$\frac{dn}{dt} = C_s \left(\frac{D_s A}{\delta}\right) \quad \text{Eq. 1}$$

For Experiment 1 the TWA-TFME embodiment of the invention was employed for the determination of UV-blocking agents in river water, on-site sampling was performed with a retracted sampler and an open bed device. Three disassembled retracted devices with a 10 mm diffusion path were transported to the sampling location in appropriate containers to ensure that individual passive sampling devices remained isolated from the environment and each other during storage, transport to the deployment site, and return to the laboratory following retrieval. They were assembled under ultrapure water in the sampling location, and the opening of the device was covered by copper mesh in order to prevent biofouling from the sampling environment. On the other hand, three open bed C18 TF-SPME devices were loaded with calibrant and wrapped with aluminum foil, then transported in a cold box filled with dry ice to the sampling location. Upon arrival, TF-SPME samplers were inserted individually into copper bags to secure them in the sampling environment. All samplers were then placed in the plastic cage and deployed at the sampling site. Sampling time was 90 days for the retracted devices and 5 days for the open bed configuration. Once the sampling time had elapsed, the samplers were retrieved and rewrapped in aluminum foil, placed in the dry ice box, and transported to the laboratory. The analytes were desorbed in 1800 μL of a desorption solvent consisted of methanol/acetonitrile/isopropanol (50/25/25, v/v/v) for 30 min. The desorption solvent was evaporated under nitrogen stream and residue was reconstituted in 300 μL of methanol/water (50/50, v/v), then analyzed with the LC-MS/MS.

Laboratory calibration of the TWA sampler was performed by placing nine samplers in a aqueous standard generator system simultaneously for different time intervals. The samplers were retrieved on the 30th, 56th and 70th day. Since the diffusion of analytes in stagnant water between the thin film and the opening of the sampler is controlled by the mass-transfer, the diffusion is assumed to follow Fick's first law under a steady state condition; as such, the mass uptake can be calibrated by use of Fick's first law of diffusion (Eq. 2).

$$C = nZ/ADt \quad \text{Eq. 2}$$

Where C is the TWA concentration, n is the amount of analyte extracted, Z is the diffusion path length, A is the cross-sectional area of the opening, D is the diffusion coefficient, and t is sampling time. The diffusion coefficient of neutral and charged organic molecules in water can be obtained empirically. The ratio of theoretical sampling rate (RS) to analyte diffusion coefficient (D) depends on the geometric configuration of the sampler only, that is, (RS/D)=A/Z. The ratio of theoretical sampling rate to the experimental sampling rate (RS) should be equal to 1, which verifies that the sampler can be calibrated by diffusion-based calibration. For this purpose, samplers with three different diffusion paths were exposed in the sampling chamber with known concentrations of analytes for a defined time. The device was calibrated at 24±1° C., and the water temperature in the sampling site varied from 19 to 22° C. during the sampling. The effect of temperature on the sampling rate was within the predetermined experimental error limits in this experiment. However, if the temperature of the sampling site is significantly different than the temperature that the device is calibrated with, the diffusion coefficient of a given analyte should be recalculated, taking into consideration the dynamic viscosity of water at the alternate temperature.

The zero sink test for the HLB coating was performed as described in the experimental section. A t test was conducted to compare the results obtained for the different approaches, indicating that there was no statistically significant difference ($\alpha$=0.05) between amounts of extracted analytes for intermittent and continuous exposure. Thus, it could be concluded that the HLB coating behaved as a zero sink for all of the target analytes due to its strong affinity toward the analytes and the large capacity of the coating via surface adsorption. The amount of analytes adsorbed on the surface of the coating after 70 days of TWA sampling time corresponded to less than 5% of equilibrium amounts. The extraction time profiles of the analytes were investigated from 30 to 9600 min in triplicate using HLB TF-SPME in sampling chamber of aqueous standard generator system in order to find the equilibrium time and subsequently the extracted amount at equilibrium. The amounts of analytes extracted to the coating at equilibrium were 1200, 8000, 1700, 1350, and 2200 ng for Ben-1, Ben-2, Ben-4, PBSA, and Ben-3, respectively. For the thin film retracted device with a diffusion path length of 10.0 mm, the response time for the analytes was 4-10 h. The response time is defined as the average dwelling time of an analyte inside the diffusion path, which can be calculated using Eq. 3.

$$\text{Response time} = Z^2/2D \quad \text{Eq. 3}$$

Where Z is the diffusion path length (in cm) and D is the diffusion coefficient (in cm$^2$/s). Nevertheless, response time is negligible in comparison to sampling time, which could be as long as 90 days. To confirm the third condition mentioned before, a face velocity effect test was carried out in a well-agitated sampling chamber (800 rpm, calculated linear flow rate was ~50 cm/sec) and in a mixing chamber where the linear velocity was low (0.15 cm/sec). Three samplers were exposed in each chamber for 30 days. The obtained results showed that there was no significant difference between accumulated masses in the samplers for both conditions. This is a desired feature of the sampler for on-site applications, where convection conditions are typically variable and difficult to measure and calibrate for.

The two TWA samplers developed and validated in the laboratory were subsequently used for an on-site investigation. The downstream of the Doon (Kitchener) municipal wastewater treatment plant, which reaches Grand River (Southern Ontario, Canada) (43° 28'23.21"N; 80° 28'40.4"W), was selected for deployment of the devices as the indirect input of this contamination stems from effluent of a wastewater treatment plant. Sampling time of the retracted device was selected in view of typical concentration levels found for the analytes in pre-screened investigations as well as the detection limit of the LC-MS/MS instrument. Two samplers were deployed at the same time and the sampling time for retracted and open TF-SPME TWA samplers was set as 90 and 5 days, respectively. Average concentrations and relative standard deviations (RSD) of spot sampling and TWA sampling results are shown in Table 2. The TWA concentrations of the analytes were calculated with the use of Eq 2. The results obtained by the two methods are similar. Ben-1, Ben-3, Ben-4, and PBSA were detected in spot sampling, while only PBSA and Ben-4 were detected in TWA sampling. This is due to the low sampling rate of the device, and the low concentrations of Ben-1 and Ben-3 in river water. No biofouling of the phase was observed for HLB TF-SPME. The stability of the analytes on the extraction phase was validated in laboratory by two months exposure of analyte preloaded thin films to collected river water and compared to analyte preloaded control thin films which were immersed in pure water with pH and ionic strength adjusted to reflect typical river water. All experiments were performed in triplicate, and the results of the two studies were compared by t test. No statistical differences observed ($\alpha$=0.05) between the two sets of data which agrees with previous studies where it was reported that the analytes are more stable in the extraction phase rather than in the sample matrix. Three of the open bed samplers were retrieved after 2, 5, and 10 days. Analysis showed that 50% of the calibrant was lost within 5 days of sampling, which was determined to be the optimum time for measuring TWA concentrations. TCS, OCR, and Ben-3 were detected and quantified by eq 10, with results shown in Table 2.

In addition to TWA sampling with open bed TF-SPME, spot sampling, conducted by grab sampling with a bottle, was investigated for determination of the concentrations of analytes over the TWA sampling time. Although the used sampler has the lowest limits of detection for OMC, TCC and BM-DBM, these compounds were not detected in the sampling site. In addition to the potential effects of biodegradation and photodegradation, the lack of detection of these analytes may be explained by their high binding coefficient to sediment, as they possess a high distribution coefficient between water and dissolved organic carbon (DOC) or particulates, caused by their high KOW value. Yet another reason would be effective elimination of these compounds in wastewater treatment plants. Both formats of TF-SPME presented in this research can measure the free concentrations of analytes in complex matrices when DOC or particulates are present. Binding to organic carbon lowers the free fraction of organic contaminants the sampling uptake of highly bound analytes. Moreover, procedural and field blank samples were analyzed, and none of the analytes under study were detected. The data in Table 2 shows good agreement between the TWA passive sampling methods and relevant spot sampling results. The targeted analytes were also reported by other researchers in different sampling sites known to hold comparable concentrations to those detected in Grand River, as reported in this research. Additionally, possible biofouling on the sampling devices was also investigated. As previously mentioned, the samplers were protected in copper mesh bags in order to prevent biofouling. In addition, the retracted devices that were deployed for a longer time were further protected from biofouling by being retracted in the sampler. Moreover, polyacrylonitrile, which was used to immobilize HLB and C18 particles, serves as a biocompatible glue and membrane, providing additional protection from biofouling. Thus, in none of the deployed devices was biofouling observed. A scanning electron microscopy (SEM) image, revealed that the devices were free from any biofouling after on-site deployment.

TABLE 2

Field Sampling Results of Retracted TF-SPME and Open Bed TF-SPME TWA Samplers in Grand River, ON concentration

| One-calibrant kinetic calibration | Concentration (ng L$^{-1}$) | | | | | |
|---|---|---|---|---|---|---|
| | OCR (RSD, %) | TCS (RSD, %) | Ben-3 (RSD, %) | OMC (RSD, %) | TCC (RSD, %) | BM-DBM (RSD, %) |
| Open bed C18 TF-SPME TWA sampler (n = 3) June 13-17 | 90 (9) | 36 (5) | 27 (19) | <0.04 | <0.01 | <0.01 |
| Grab sampling (n = 6) June 13, June 17 | 130 (15) | 50 (15) | 28 (10) | <20 | <0.1 | <3 |
| Procedural blank Field blank | <1000 <0.2 | <100 <0.2 | <1000 <0.5 | <500 <0.04 | <1 <0.1 | <160 <0.01 |

| Grab sampling with open bed HLB TF-SPME (equilibrium sampling) | Concentration (ng L$^{-1}$) | | | | |
|---|---|---|---|---|---|
| | Ben-1 (RSD, %) | Ben-3 (RSD, %) | Ben-4 (RSD, %) | PBSA (RSD, %) | Ben-2 (RSD, %) |
| June 13-22 (n = 3) | 5 (7) | 23 (12) | 4500 (12) | 3300 (20) | <0.5 |
| July 15-24 (n = 3) | 5 (13) | 17 (11) | 6000 (11) | 4000 (12) | <0.5 |
| August 12-21 (n = 3) | 6 (8) | 19 (6) | 6600 (15) | 4900 (11) | <0.5 |

TABLE 2-continued

Field Sampling Results of Retracted TF-SPME and Open Bed
TF-SPME TWA Samplers in Grand River, ON concentration

| | | | | | |
|---|---|---|---|---|---|
| Ave | 5 | 20 | 5700 | 3700 | <0.5 |
| Retracted HLB TF-SPME TWA Sampler (n = 3) June 13 - September 13 | <700 | <800 | 5400 (15) | 4000 (12) | <130 |
| Procedural blank | <500 | <1000 | <2500 | <500 | <100 |
| Field blank | <700 | <800 | <160 | <130 | <500 |

For Experiment 2 the in bottle TF-SPME embodiment of the invention was employed for the determination of pesticides in surface water. The designed in-bottle TF-SPME embodiment (FIG. 2) allows for extraction of compounds from the moment that the bottle is filled with water sample in the field. Given that the time needed to transport samples from site to laboratory, as well as the waiting time for analysis can both significantly vary for different samples, it is necessary that all experiments are conducted in the equilibrium regime. Evaluation of extraction time profiles was carried out by spiking nanopure water with the selected compounds, ten pesticides from different classes and polarities, at a concentration of 100 ng $L^{-1}$. Three internal standards, 3,5-DCP-d3, Trifluralin-d14, and Metolachloe-d6 were also added to the sample. The orbital shaker was selected as apparatus to agitate the water sample in the 1 L bottle at 200 rpm. Extraction time profiles were investigated from 30 min to 4 days, with results showing that the majority of the studied compounds reached equilibrium after one day. To assure equilibration of all compounds, a period of three days was selected as extraction time for further evaluation of the method. All analyses of the in-bottle TF-SPME devices were performed an Agilent 6890-5973n GC/MS. Validation of the method was based on an industry standard validation protocol, and involved four steps: evaluation of method blank and carryover; limit of detection (LOD) and quantitation (LOQ); calibration curve and linear range; and finally, precision and accuracy of the method at different concentration levels.

At first, a blank of the method was evaluated by analysis of nano pure water, using a PDMS/DVB thin film device under the previously selected conditions (i.e. three-day as extraction time, under 200 rpm using orbi-shaker). Newly prepared thin film and clean bottles were used so as to ensure no carryover from previous experiments. The obtained results showed that most of the targeted pesticides were present in nano pure water at pg $L^{-1}$ and low ng $L^{-1}$ levels.

In our previous study, nano pure water was identified as a "non-detect" for the selected pesticides due to the use of a smaller sample volume (30 mL), as well as the shorter extraction time (30 min) selected for that application. However, in the current study, given the larger sample volume, 1 L, and equilibrium time of extraction (3 days), significant enhancement in sensitivity was achieved. Therefore, the pre-concentration of compounds attained by TFME from large volumes of sample at equilibrium conditions, coupled with the cryofocusing in the TDU/CIS system in splitless mode allowed for a sensitive method able to detect ultra-trace amounts of the studied compounds. Several experiments were performed to confirm that the blank of the method was acceptable but are not detailed here.

After evaluation of blank and noise levels, LOD and LOQ values were obtained, using an S/N of 3 and 10, respectively. As shown in Table 3 and Table 4, LOD and LOQ values in low ng $L^{-1}$ were achieved by the in-bottle TFME method, in 2-3 orders of magnitude higher sensitivity than that obtained by EPA method 8270 where limits of detection are based on the standard deviation of low level analyses. Successively, a calibration curve was obtained using weighted linear regression. Good linearity was achieved in the range of 3-1000 ng $L^{-1}$, with $R^2$ >0.99 for most of the compounds. Accuracy and repeatability of the developed method were investigated at two levels of concentration, with acceptable accuracies in the range of 71-124%, and RSD % between 1-21% obtained for the selected compounds. Finally, the method was evaluated by the split blind analyses of four surface water samples fortified with the selected pesticides. The bottle was completely filled with surface water samples, and quantitation was performed using the external calibration method. The pH of surface water samples was adjusted with phosphate buffer (pH ~5.5) to match the nano pure water calibration. For future studies, in cases where filling the bottle to full capacity (1 L) might prove difficult, the amount of the sample can be calculated by weighting the bottle.

TABLE 3

In-bottle TFME Method validation data summary

| | | | | | | | Accuracy (%) | | RSD % | |
|---|---|---|---|---|---|---|---|---|---|---|
| Pesticides | LOD ng $L^{-1}$ | LOQ ng $L^{-1}$ | LDR ng $L^{-1}$ | $R^2$ | Slope | Intercept | 30 ng $L^{-1}$ | 300 ng $L^{-1}$ | 30 ng $L^{-1}$ | 300 ng $L^{-1}$ |
| Cyanazine | 3 | 10 | 10-300 | 0.9983 | 0.007 | −0.003 | 96 | 73 | 6 | 17 |
| Methyl-parathion | 30 | 100 | 100-1000 | 0.9907 | 0.011 | −0.354 | NA | 126 | NA | 6 |
| Alachlor | 3 | 10 | 10-300 | 0.9982 | 0.014 | −0.018 | 91 | 96 | 21 | 6 |
| Metolachlor | 1 | 3 | 3-300 | 0.9994 | 0.041 | 0.001 | 90 | 115 | 3 | 14 |
| 2,4,6-TCP | 3 | 10 | 10-1000 | 0.9993 | 0.041 | −0.170 | 93 | 101 | 7 | 7 |
| Diazinon | 30 | 100 | 100-1000 | 0.9983 | 0.028 | −1.745 | NA | 112 | NA | 19 |
| 2,3,4,6-TeCP | 1 | 3 | 3-1000 | 0.9996 | 0.040 | −0.065 | 86 | 124 | 9 | 20 |
| Chlorpyrifos | 4 | 10 | 10-500 | 0.9982 | 0.012 | −0.028 | 91 | 91 | 9 | 6 |
| Trifluralin | 1 | 3 | 3-500 | 0.9997 | 0.023 | −0.025 | 93 | 110 | 3 | 1 |
| Triallate | 1 | 3 | 3-500 | 0.9928 | 0.037 | −0.054 | 109 | 110 | 12 | 9 |

TABLE 4

Comparison of the method detection limit of the studied pesticides obtained by the developed methods and the standard method

| Analytes | In-bottle TFME* (ng L$^{-1}$) | Drill-based TFME* (ng L$^{-1}$) | LLE** (US EPA 8270) (ng L$^{-1}$) |
|---|---|---|---|
| 2,4,6-TCP | 10 | 100 | 500 |
| 2,3,4,6-TeCP | 3 | 250 | 500 |
| Trifluralin | 3 | 50 | 1000 |
| Diazinon | 100 | 1000 | 1000 |
| Triallate | 3 | 50 | 1000 |
| Methyl parathion | 100 | 1000 | 1000 |
| Alachlor | 10 | 100 | 500 |
| Metolachlor | 3 | 250 | 500 |
| Chlorpyrifos | 10 | 1000 | 1000 |
| Cyanazine | 10 | 100 | 1000 |

*The results obtained using bench-top GC/MS instrument and based on S/N = 10

Table 5 presents a comparison of the results obtained by both methods, showing distinctive features of the current study in terms of sensitivity and accuracy. The first feature is related to the high sensitivity of the method, capable of quantitation of the selected compounds even at the low nanogram per liter level, while the LLE method was only able to quantify compounds mainly present at the microgram per liter level. While the current method detection limit of LLE meets US EPA requirements, it is nonetheless always beneficial to push down LOQ levels to lower concentrations that allow the method to be more universally well received, as well as applied in simultaneous determinations of a wide range of compounds. Such a feature is particularly relevant for compounds characterized by lower MCLs of US EPA in some other agencies such as the EU. Further, in the LLE technique, analytes need to be present in the medium in their neutral form due to the exhaustive calibration nature of this technique; as such, for pesticides that contains acidic, basic, and neutral (ABNs) compounds, three extractions need to be performed at different pH levels so as to match each condition. Accordingly, the addition of these extraction steps makes the method cumbersome and time consuming, while the use of sodium hydroxide and hydrochloric acid adversely affect the greenness of the method. On the other hand, for TFME analysis, there is no need for adjustment of pH as long as sensitivity is not an issue, as the method is based on microextraction calibration; as such, only the pH and temperature of the sample and calibration curve should be matched.

TABLE 5

Split sample analyses of surface water samples by in-bottle TFME and US EPA 8270 methods

| Pesticides | SW1 (fortified at 900 ng L$^{-1}$) | | SW2 (fortified at 190 ng L$^{-1}$) | | SW3 (fortified at 62.5 ng L$^{-1}$) | | SW4 (fortified at 300 ng L$^{-1}$) | |
|---|---|---|---|---|---|---|---|---|
| | TFME Conc. | LLE Conc. | TFME Conc. | LLE Conc. | TFME Conc. | LLE Conc. | TFME Conc. | LLE Conc. |
| Cyanazine | NA | ND | 210 | ND | 74 | ND | 257 | ND |
| Methyl-parathion | 938 | ND | 326 | ND | NA | ND | 460 | ND |
| Alachlor | NA | 860 | 164 | ND | 49 | ND | 195 | ND |
| Metolachlor | NA | 880 | 182 | ND | 69 | ND | 239 | ND |
| 2,4,6-TCP | 931 | 620 | 191 | ND | 59 | ND | 307 | ND |
| Diazinon | 1150 | ND | 248 | ND | NA | ND | 286 | ND |
| 2,3,4,6-TeCP | 936 | 750 | 183 | ND | 50 | ND | 340 | ND |
| Chlopropyrifos | NA | ND | 359 | ND | 80 | ND | 514 | ND |
| Trifluralin | NA | ND | 307 | ND | 76 | ND | 530 | ND |
| Triallate | NA | ND | 291 | ND | 70 | ND | 527 | ND |

Table 5 also shows the achievement of accuracies higher than 85% (except for one point) for the studied compounds in surface water samples, even for triallate and trifluralin, which have log p values of 6.18 and 5.41, respectively. As such, it can be concluded that by avoiding the use of sub-samples, even in cases where compounds adsorb on the surface of the bottle, high accuracy in quantitation can be achieved by the method. As the procedures followed to obtain both the calibration curves and to carry out the analysis of real samples are matched, the free concentrations of the compounds under study can be assumed to be similar, leading to improved accuracy of quantitation. A comparison between the results obtained in the present study and findings from our previous study also shows improvement in accuracy for hydrophobic compounds, from the range of 40-70% to the acceptable range (i.e. ≥70%). While the accuracy of the method for a few compounds was observed at 150%, such figures can be adjusted in future studies by selecting a deuterated internal standard for each compound to accurately correct instrumental fluctuations.

For the on-site TFME comparison, the drill-TFME method was optimized in the laboratory to evaluate influential parameters, including the extraction time profile and agitation rate of the drill. The agitation rate was the first parameter investigated, as it controls the thickness of the boundary layer, and affects the mass transfer of compounds to the coating. In the pre-equilibrium regime, improved sensitivity is expected to be achieved at higher agitation rates due to a decrease in the thickness of the boundary layer. Application of high agitation rates are beneficial for on-site extractions, since a short extraction is preferred due to practical limitations (e.g. lifetime of the battery, the difficulty of sampling when the sample is not easily accessible). In view of this, agitation rates in the range of 500-3000 rpm were investigated in 1 L of nano pure water spiked with the target pesticides at 1 µg L$^{-1}$. The highest sensitivity increases were observed for most compounds at 2000 rpm.

An extraction time profile was then obtained using the optimized stir rate of 2000 rpm in 1 L nano pure water spiked at 1 µg L$^{-1}$. after three hours, all spiked compounds were shown to reach equilibrium. However, as previously mentioned, a shorter extraction time needed to be selected so as to simplify the on-site TFME procedure. Therefore, 10 minutes was selected as the extraction time for further evaluation of the methods.

Table 4 shows the LOD and LOQ values of the drill-based TFME method (in the range of 20-300 ng L$^{-1}$) using a 10 min extraction time and 2000 rpm agitation rate. Quantitation was performed using a Gerstel TDU-CIS equipped Agilent 6890-5973n GC/MS. This table also compares the method detection limits of the in-bottle TFME, drill TFME, and US EPA 8270. Quantitation can be performed either by using an external calibration curve obtained under a negligible depletion condition or by obtaining the sampling rate of individual compounds. It is worth mentioning that, at the negligible depletion condition, extracted amount is independent from sample volume and therefore calibration curve obtained in lab can be used for on-site analysis and quantitation from river.

For Experiment 3 the magnetic locking coated bolt embodiment of the invention was employed for the screening and on sampler storage stability of unknown contaminants from waste water effluent. In order to confirm that the self-sealing sampler design was capable of stabilizing extracted compounds on the sorbent coating for purposes of multi-variate identification, real samples were taken using 3 different devices (18 coated bolts total) and then stored at varied conditions for up 12 days. The real world samples were taken at the outflow pipe of the Galt Wastewater Treatment Facility on the Grand River (Cambridge Ontario). Ambient river temperatures were measured to be 6.5° C. while the temperatures at the outflow fluctuated slightly around 20° C. Samplers were deployed on-site via kayak and sampling was performed for 1 hour. Following sampling, the devices were then closed into their sealed position and transported back to the laboratory. Solvent desorption was then immediately performed on 4 of the 18 coated bolts while the remaining devices were stored within the self sealing sampler bodies at room temperature for 3 days, room temperature for 12 days, and in the −80° C. freezer for 12 days. Analyses were performed on a high resolution HPLC-MS (Thermo Accela-orbitrap) instrument and multivariate data processing was used to identify insignificance of storage time As the coated bolt samplers were designed with the explicit purpose of stabilizing extracted compounds on the sorbent coating for extended periods at ambient conditions it was decided to perform identical real world extractions from the outflow pipe of the Gall Wastewater Treatment facility with multiple devices that were then stored for varying amounts of time and conditions. This storage stability was validated using one-way ANOVA at a 95% level of confidence (Table 6) showing that for the 10 selected features there were no significant difference in the amount of analyte remaining on the sorbent coating, even following 12 days of room temperature storage. This is promising as even though these features were selected randomly, preference was given to compounds with lower molecular weight as these would likely be the most volatile and hence least stable on a given extraction phase. Additionally, as the pooled QC was prepared by mixing a small portion from each extract, it was encouraging to see that it gave similar signal to that of the samples. However, it was apparent that the pooled QC data, which is generated from 7 replicate injections from the same vial, gave noticeably less error than the pooled data from each of the individual coated bolts with % RSD's ranging from 5-12% and 9-20% respectively. Although potentially indicating that there could be some variation in terms of inter-bolt reproducibility, this variability is well within an acceptable range for on-site sampling methodologies.

Figure 6:
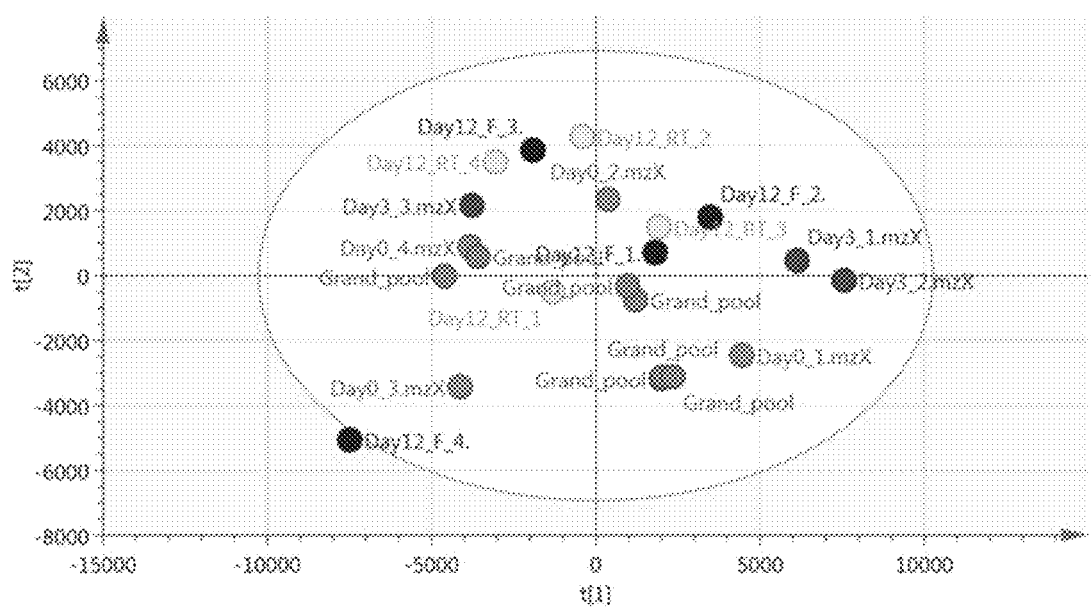
FIG. 6 Multivariate comparison (PCA) of replicate samples from the magnetic locking coated bold TF-SPME embodiment with samples that had no long term storage, 3 days of room temperature storage, 12 days of room temperature storage, 12 days of storage at −80° C., and the pooled QC injection. No separation patterns were observable, even for the pooled QC injection as all samples were nearly identical.

As to ensure that the noted reproducibility wasn't just associated with the 10 randomly selected features, principle component analysis was also applied to the dataset to see if any grouping could be observed between coated bolts from different storage conditions. Appropriately, no clustering was observed between samples in the related principal component analysis (PCA) plot indicating that any separation among samples was likely due to random background noise. This is to be expected as multivariate approaches base separation on the most significant features present in a given dataset. When no actual statistical differences exist between different samples the PCA algorithm will begin assigning random noise as the most significant driving factor for sample separation resulting in a randomly distributed PCA plot like that seen in FIG. 6. Furthermore, because the samples were so similar, even the pooled QC data was found to exhibit poor grouping on the PCA plot, despite good performance of instrumental QC.

Although feature identification was not the focus of this study, the empirical molecular formula and likely compound class is also given in Table 6. The empirical formulas given were assigned based on exact mass matching on the Metlin database and all possibilities within +1-5 ppm of the exact mass were listed. Exact identification for compounds this simple is not possible based on exact mass matching alone, hence only likely compound type is presented herein. One interesting identification however was that of the most volatile analyte listed, the protonated xylene like compound with exact mass 107.0858. Although, very common water contaminants these compounds are known to exhibit poor ionization efficient with electrospray ionization techniques (ESI) and are typically considered more GC-MS amenable. More interestingly however, HPLC-MS methods have already been developed for the determination of various benzothiazoles and benzotriazoles as common wastewater contaminats. These classes of compounds were tentatively identified in this dataset. However, as previously mentioned, any of these tentative ID's are speculative without appropriate MS" validation or standard confirmation but this results remains interesting nonetheless.

TABLE 6

ANOVA testing at 95% confidence demonstrating 12 day room temperature storage stability of extracted compounds on the HLB/PAN coated bolt magnetic bolt sampler ($F_{crit}$ = 3.71)

| Exact Mass | RT | Empirical formula | Tentative Compound class | F Value | % RSD |
|---|---|---|---|---|---|
| 107.0858 | 19.93 | C8H10 | a xylene | 2.08 | 20 |
| 120.0559 | 10.21 | C6H5N3 | benzotriazole or similar | 0.92 | 16 |
| 135.0749 | 11.71 | No match | No database match | 0.77 | 16 |
| 143.1069 | 13.49 | C8H14O2 | a carboxylic acid | 1.20 | 16 |
| 182.0095 | 16.92 | C8H7NS2 | a Methylthio-benzothiazole | 1.47 | 13 |
| 189.1639 | 19.93 | C5H6ClN3O | a Chloro-methoxypyrazin-amine | 3.71 | 17 |
| 199.0968 | 11.59 | C8H18O5 | Tetra ethylene glycol | 1.87 | 19 |

TABLE 6-continued

ANOVA testing at 95% confidence demonstrating 12 day room temperature storage stability of extracted compounds on the HLB/PAN coated bolt magnetic bolt sampler ($F_{crit} = 3.71$)

| Exact Mass | RT | Empirical formula | Tentative Compound class | F Value | % RSD |
|---|---|---|---|---|---|
| 213.0429 | 18.84 | C10H14O4 | a carboxylic acid | 2.03 | 16 |
| 309.2039 | 21.24 | C7H16OS3 or C6H12O6S or C9H9ClN2O2 | | 1.70 | 13 |
| 315.0098 | 21.63 | N/D | Multiple possibilities | 0.40 | 9 |

For Experiment 4 the self-sealing coated bolt embodiment, designed for ROV submersibles, was employed for the differentiation of significant features originating from deep sea hydrothermal vents. As a means to demonstrate the full robustness of the self-sealing coated bolt sampler design, various samplers were deployed on two separate dives for the on-site SPME extraction of hydrothermal vents. The first ROV sampling was performed at a depth of 1518 m on a hydrothermal vent located on the edge of the El Gordo seamount which possessed a great deal of visible aquatic life. Three separate samplers were taken on the dive allowing for the sampling of A: an active hydrothermal vent B: Ambient ocean water to serve as a control and. C: an unused sampler to serve as a method blank. Unfortunately, due to a miss-communication between our research teams and the ROV crew, the sampler was only exposed for a total of 15 seconds in both the control location and active hydrothermal vent. The control sample was taken just a few meters above the hydrothermal vent which was not considered ideal as some of the hydrothermal vent features to could have been also extracted by the control sampler. Follow sampling, a given ROV-TF-SPME device was then placed in an enclosed ROV "bio-box" for the remainder of the dive and ascent. Once shipside, these devices were then stored at −80° C. within the on-ship freezer for the remainder of the voyage. Finally, upon returning to port, the samplers were then shipped under dry-ice to the University of Waterloo for desorption and analysis.

The second ROV-SPME sampling was performed at a depth of 2929 m at an unspecified vent along the NW Rota dive site. Sampling of the active vent site was performed for exactly 6 minutes, 24 seconds with vent temperatures measured at 17.3° C. The control extraction of the ambient sea water was performed during ROV ascent and lasted exactly 6 minutes with ambient water temperatures measured as 1.5° C. Furthermore, much like the first ROV sampling a third, unused, SPME device was carried on-board the submarine to serve as a method blank for the dive. Follow sampling, a given ROV-SPME device was then placed in an enclosed ROV "bio-box", for the remainder of the dive and ascent. Once shipside, these devices were then stored at −80° C. within the on-ship freezer for the remainder of the voyage. Finally, upon returning to port, the samplers were then shipped under dry-ice to the University of Waterloo for desorption and analysis.

Figure 7:
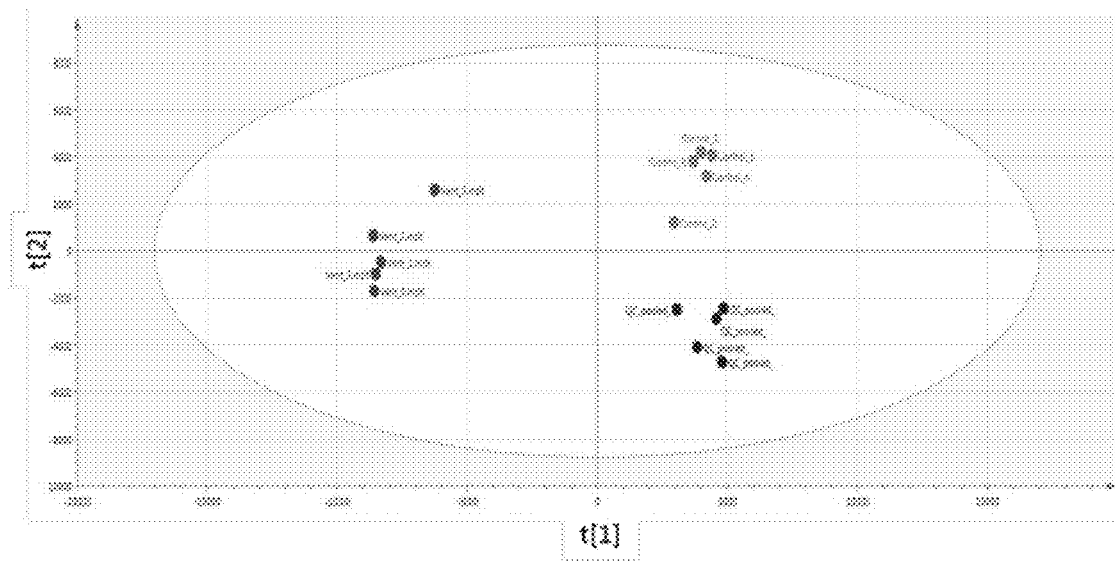
FIG. 7 Multivariate comparison (PCA) of replicate samples from the ROV deployed self-sealing coated-bold TF-SPME embodiment with samples that correspond to extractions from the El-Gordo hydrothermal vent sample, the control sample and the validating pooled QC data. Despite 15 second sampling excellent grouping and separation was observed for the samples.

Multiple self-sealing TF-SPME coated bolt ROV operable devices were prepared and deployed on 2 separate dives of ROV submersible submarines for the untargeted investigation of deep sea hydrothermal vents. As previously noted, the first dive was performed at the El Gordo hydrothermal seamount 2.9 km deep in the Pacific Ocean. Unfortunately, due to a miscommunication between our joint team and the ROV operator team, the sorbent coating was only exposed to the vent and control samples for 15 seconds. Despite this incredibly short sampling time it was pleasantly surprising to see excellent separation between the control and vent locations when unclassed principle component analysis was performed (FIG. 7). This could be attributed to the large 250 mm² surface area of the coated bolts. Being 22.5 times larger than that of a classical SPME fibre, response would theoretical be the same as if a 5.63 minute fibre based extraction was performed instead. This result very much highlights just how important sampler design can be in saving an otherwise botched sampling opportunity. However, it is worth noting that only 5 of the 6 replicate samples from each site could be reliably plotted as 2 of the non-recessed coatings were found to be damaged as a likely result of scraping on the sampler body. It is for this reason that recessed coatings were used on future dives. After confirming reasonable unclassed separation of the samples, an OPLS-DA classed model was then used to generate an S-plot and related VIP list to differentiate significant features from the samples. Over 50 features were found to be unique to the vent site indicating successful differentiation of significant features between the active vent and control site.

Figure 8:
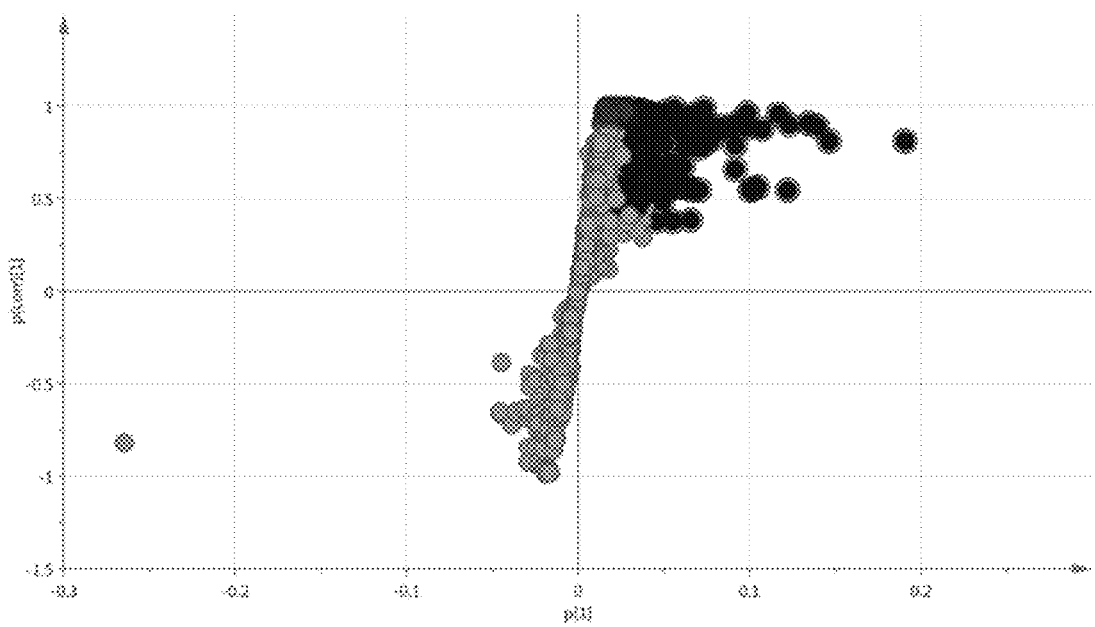
FIG. 8 S-Plot generated from the classed multivariate separation of data generated from the ROV deployed self-sealing coated-bold TF-SPME embodiment with features that correspond to extractions from the NW-Rota hydrothermal vent sample highlighting features that were statistically larger in the vent sample. Only PFP positive results were shown.

Much better communication was established between our research teams and the ROV crew during the second dive. Although this sampling did not necessarily give ideal choice of the vent location due to constraints encountered by the ROV team, the samplings were performed properly, giving 6 minutes at both the control and vent site which had measured temperatures of 1.53° C. and 20.4° C. respectively. Furthermore, the control sampling was performed during ROV ascent, well away from the sampling site. The chosen vent site, had very little visible life growing immediately around the hydrothermal plume, however there was evidence of many shrimp living in proximity to this vent, likely feeding on microorganisms from this plume. In terms of multicomponent separation the PCA plot still indicated good separation between the control and vent samples, however grouping of the 6 vent samples was shown to be broad. Upon reviewing the dive video it was apparent that one side of the sampler was more directly inserted into the hydrothermal plumb likely resulting in this discrepancy. Furthermore, this variation can still be seen even when the samples were grouped by class using the OPLS-DA model. However, it is worth noting that despite this weaker clustering, samples could still be fully separated along the first principle component, t[1], of the OPLS-DA plot indicating that the loading of features on the generated S-plot shown in FIG. 8 would still be reliable. A similar trend could be seen when the samples were instead ionized in negative mode. Over 300 features were found to be unique to the vent site indicating successful differentiation of significant features between the active vent and control site.

The invention claimed is:

1. A device for carrying out solid phase microextraction of analytes contained in a fluid carrier, the device comprising:
    (a) a container, and a cap sized and shaped to fit the container, the cap being removably connectable to the container by way of corresponding screw threads;
    (b) a metal blade or carbon fabric;
    (c) a thin film extraction coating on at least a portion of the metal blade or carbon fabric; and
    (d) a support attached to and extending from the cap, wherein the coated metal blade or carbon fabric is attached to the support, and the coated metal blade or carbon fabric is located within the container when the cap is screwed on to the container.

2. The device as claimed in claim 1, wherein the thin film extraction coating is formed of a material selected from the group consisting of non-polar and polar coatings.

3. The device as claimed in claim 1, wherein the thin film extraction coating is formed of a material selected from the group consisting of poly(dimethylsiloxane), poly(divinyldibenzene), derivatized poly(divinyldibenzene), carbon, monomers comprising ionomers produced by copolymerization of fluorocarbon with a carboxylic acid or ester, nylon, florocarbon polymers, polyethylene glycol, silicone, polyimide, polyacrylonitrile, octadecyltrichlorosilane, polymethylvinylchlorosilane, hydrophilic-lipophilic balanced polymers, poly(divinylbenzene-co-N-vinylpyrrolidone), graphene, carbon nanotubes, liquid crystalline polyacrylates, grafted self-assembled monolayers, and inorganic coatings.

4. The device as claimed in claim 1, wherein the thin film extraction coating has a morphology that provides matrix compatibility.

5. The device as claimed in claim 1, wherein the container is a bottle.

6. The device as claimed in claim 1, wherein the container is made from a soft metal, glass, or plastic.

7. The device as claimed in claim 1, wherein the support comprises at least one thread.

8. The device as claimed in claim 7, further comprising a stabilizing weight connected to the at least one thread.

9. The device as claimed in claim 8, wherein the coated metal blade or carbon fabric is attached to the at least one thread between the cap and the stabilizing weight.

10. The device as claimed in claim 1, wherein the support comprises a rod.

11. The device as claimed in claim 1, comprising a plurality of coated metal blades or carbon fabrics, wherein at least two of the thin film extraction coatings are different.

12. A method of determining the concentration of at least one analyte of interest in a fluid carrier, the method comprising:
    filing a container with the fluid carrier,
    closing the container with a cap by screwing the cap onto the container by way of corresponding screw threads, the cap comprising a support that supports a metal blade or carbon fabric, the metal blade or carbon fabric being at least partially coated with a thin film extraction coating, to bring the coated metal blade or carbon fabric into contact with the fluid carrier,
    maintaining contact between the fluid carrier and the thin film extraction coating for a sufficient time to adsorb at least some of the at least one analyte from the fluid carrier onto the coating,
    unscrewing the cap from the container and removing the coated metal blade or carbon fabric from the container,
    desorbing at least some of the adsorbed analyte from the coating into an analytical instrument, and
    determining the identity and concentration of the at least one analyte.

13. The method as claimed in claim 12, wherein the support supports a plurality of coated metal blades or carbon fabrics.

14. The method as claimed in claim 12, wherein the container is a bottle or a bag.

15. A cap sized and shaped to fit a container, the cap comprising screw threads and a support that supports a metal blade or carbon fabric, wherein the metal blade or carbon fabric is at least partially coated with a thin film extraction coating for carrying out solid phase microextraction of at least one analyte contained in a fluid carrier, and wherein the metal blade or carbon fabric is supported in the fluid carrier when the cap is removably connected to a container containing the fluid carrier by way of corresponding screw threads.

16. The cap as claimed in claim 15, wherein the support comprises at least one thread.

17. The cap as claimed in claim 16, wherein the at least one thread is attached to a stabilizing weight.

18. The cap as claimed in claim 17, wherein the metal blade or carbon fabric is attached to the at least one thread between the cap and the stabilizing weight.

19. The cap as claimed in claim 15, wherein the container is a bottle.

* * * * *